United States Patent [19]

Daniels

[11] 4,050,993
[45] Sept. 27, 1977

[54] DISTILLATION OF READILY POLYMERIZABLE ETHYLENICALLY UNSATURATED COMPOUNDS

[75] Inventor: Calvin L. Daniels, Big Spring, Tex.

[73] Assignee: Cosden Oil & Chemical Company, Big Spring, Tex.

[21] Appl. No.: 288,138

[22] Filed: Sept. 11, 1972

[51] Int. Cl.² .......................... B01D 3/34; C07C 7/18
[52] U.S. Cl. .................................. 203/9; 260/669 A
[58] Field of Search .................... 203/8, 9, 58, 59, 70; 260/669 A, 669 R; 210/57, 58

[56] References Cited

U.S. PATENT DOCUMENTS

| 2,473,203 | 6/1949 | Howe | 203/9 |
|---|---|---|---|
| 2,867,672 | 1/1959 | Hemmerich | 260/669 R |
| 3,408,265 | 10/1968 | Ward | 203/9 |
| 3,476,656 | 11/1969 | Van Tassell | 203/9 |
| 3,523,141 | 8/1970 | Sakashita | 203/9 |
| 3,527,822 | 9/1970 | Benson | 203/9 |
| 3,629,076 | 12/1971 | Jones | 203/9 |
| 3,684,665 | 8/1972 | Abe | 203/9 |

Primary Examiner—Frank W. Lutter
Assistant Examiner—Frank Sever

[57] ABSTRACT

The present invention relates to a process for the distillation of readily polymerizable ethylenically unsaturated compounds comprising subjecting such compounds to distillation conditions in the presence of nitroso methylaniline as a polymerization inhibitor and in the absence of oxygen (air) and sulfur.

7 Claims, No Drawings

DISTILLATION OF READILY POLYMERIZABLE ETHYLENICALLY UNSATURATED COMPOUNDS

BACKGROUND OF THE INVENTION

The present invention relates to a process for the distillation of readily polymerizable, ethylenically unsaturated compounds. More particularly, the present invention relates to a process of distillation whereby the amount of polymerization of readily polymerizable, ethylenically unsaturated compounds is substantially reduced during distillation as compared to certain present methods. Still more particularly, the present invention relates to a process of distillation of readily polymerizable, ethylenically unsaturated compounds whereby the material accumulating in the bottom or reboiler area of the distillation apparatus can be reused as opposed to certain present methods wherein such bottom or reboiler area material is a high pollution waste material. Additionally, the present invention relates to a process of distillation of readily polymerizable, ethylenically unsaturated compounds whereby the rate or throughput for a given distillation apparatus can be increased over the rate at which such distillation apparatus can be operated using present methods. Further the present invention relates to a process of distillation of readily polymerizable, ethylenically unsaturated compounds whereby the distillation product is not tinted by the polymerization inhibitor utilized. Further still, the present invention relates to a process of distillation of readily polymerizable, ethylenically unsaturated compounds whereby the ease of handling of the polymerization inhibitor is substantially increased.

It is known that ethylenically unsaturated compounds such as monomeric styrene and divinylbenzene polymerize readily and that the rate of polymerization increases with increasing temperature. Inasmuch as divinylbenzene and styrene produced by common industrial methods contain reaction products, they must be subjected to separation and purification to be suitable to certain further desirable industrial uses. To prevent polymerization during such separation and purification, various prior art processes employing known polymerization inhibitors such as 4-tert-butylcatechol (TBC) and hydroquinone have been employed. However, vacuum distillation is the preferred method for the separation of unstable organic liquid mixtures and the aforementioned prior art inhibitors are effective only in the presence of oxygen. The partial pressure of oxygen in a vacuum distillation column is too low for such conventional inhibitors to be effective. Another prior art method involves the use of sulfur as the polymerization inhibitor. Although sulfur is effective in the absence of oxygen, it is not as effective as the inhibitor of the present invention and, as an additional undesirable feature, forms a high pollution valueless waste material as a bottoms product.

An example of a prior art method is found in the distillation of vinyl aromatic compounds such as divinylbenzene. In such prior art method, the mixture to be distilled generally is first contacted with the chemical polymerization inhibitor, i.e., sulfur and/or TBC. The resulting mixture containing the chemical polymerization inhibitors is then subjected to distillation conditions in the distillation apparatus. The amount of polymer formed in the distillation apparatus and in the high purity product taken therefrom is substantially higher than desired, and occasionally complete polymerization occurs inside the distillation apparatus. For instance, in the process of distilling crude divinylbenzene (a mixture containing divinylbenzenes, diethylbenzenes and monovinylbenzene) to obtain high purity divinylbenzenes, even when inhibited with sulfur and TBC, a divinylbenzene product is obtained which contains significant quantities of polymer which are difficult to separate from the divinylbenzene and detrimental to the use of such divinylbenzenes. Furthermore, the material which is removed from the bottom or reboiler area of the distillation apparatus is a high pollution sulfurous waste material which must be disposed of.

Other prior art methods utilize certain nitroso compounds as a vacuum distillation polymerization inhibitor. An example of such prior art method is found in the distillation of styrene monomer. Such prior art methods have included the use of such nitroso compound polymerization inhibitors as N,-nitroso phenylhydroxylamine (NPH) and p-nitroso-N,N,-dimethylaniline (NDMA). Although such inhibitors are effective in the absence of oxygen, they have certain disadvantages not possessed by the present invention. For example, NPH is substantially insoluble in hydrocarbons and thus, requires use of special mutual solvents in order to permit its admixture with styrene. NDMA has not been found as effective as such inhibitors as sulfur and thus, has not gained commercial acceptance.

It is now an object of the present invention to provide a new and improved process for the distillation of readily polymerizable ethylenically unsaturated compounds.

Another object of the present invention is to provide a new and improved process for the distillation of readily polymerizable ethylenically unsaturated compounds, which process results in higher recovery of the high purity unsaturated compound and produces less undesirable by-products.

Yet another object of the present invention is to provide a new and improved process for the distillation of readily polymerizable ethylenically unsaturated compounds, which process results in the production of less polymerized material in the distillation apparatus.

Still another object of the present invention is to provide a new and improved process for the distillation of readily polymerizable ethylenically unsaturated compounds, which process enables substantially increased ease of handling due to the liquid nature and ready solubility of the utilized polymerization inhibitor in readily polymerizable ethylenically unsaturated compounds.

A further object of the present invention is to provide a new and improved process for the distillation of readily polymerizable ethylenically unsaturated compounds, which process results in a clear, uncolored distillation product.

A still further object of the present invention is to provide a new and improved process for the distillation of readily polymerizable ethylenically unsaturated compounds, which process does not produce high pollution bottom or reboiler area waste material.

Yet a further object of the present invention is to provide a new and improved process for the distillation of readily polymerizable ethylenically unsaturated compounds, which process enables a given distillation apparatus to be operated at an increased rate of throughput without a reduction in efficiency.

Additional objects will become apparent from the following description of the invention herein disclosed.

SUMMARY OF THE INVENTION

The present invention, which fulfills these and other objects, in one of its embodiments is a process for the distillation of readily polymerizable ethylenically unsaturated compounds, said process comprising subjecting such readily polymerizable ethylenically unsaturated compound to distillation conditions in the presence of N,N-nitrosomethylaniline (NMA) in the absence of oxygen (air) and sulfur. In another embodiment, the present invention comprises mixing the NMA in a heavy aromatic hydrocarbon fraction having a higher boiling point than the readily polymerizable ethylenically unsaturated compound to be distilled, mixing the solution of NMA and heavy aromatic hydrocarbon fraction with the readily polymerizable ethylenically unsaturated compound to be distilled, and distilling the resultant mixture in a distillation apparatus in the absence of air and sulfur.

Through the use of the process of the present invention, the amount of polymerization occurring inside the distillation apparatus is significantly reduced. In addition, the amount of desired distillation product is increased in proportion to the decrease in the amount of polymer formation. Also, the rate of operation of a given distillation apparatus can be increased. Still further, the material accumulating in the bottom or the reboiler area of the distillation apparatus can be reused, e.g., for its fuel value or for reprocessing, as opposed to certain present methods utilizing sulfur as a polymerization inhibitor wherein such bottom or reboiler area material is a high pollution waste material.

DESCRIPTION OF THE PREFERRED EMBODIMENTS OF THE PRESENT INVENTION

The distillation process of the present invention employs N,N-nitroso-methylaniline (NMA) in the absence of oxygen (air) and sulfur to inhibit polymerization of the readily polymerizable ethylenically unsaturated compound being distilled.

The distillation technique of the process of the present invention is suitable for use in virtually any type of separation of a readily polymerizable ethylenically unsaturated compound from a mixture where such readily polymerizable unsaturated compound is subjected to temperatures above room temperature. The process of the present invention is particularly useful in vacuum distillation, the preferred method for separation of unstable organic liquid mixtures. In its most useful application, the distillation technique of the present invention is applied to the distillation of mixtures containing ethylenically unsaturated compounds such as styrene or divinylbenzene. The preferred application of the present invention is in the distillation of crude divinylbenzene or crude styrene in the absence of oxygen (air) and sulfur.

During vacuum distillation of divinylbenzene-containing mixtures and styrene-containing mixtures, the temperature of the reboiler is preferably maintained at from about 185° to about 225° F. The reboiler pressure is usually controlled at from about 10 to about 50 m.m. Hg., preferably 15 to 40 m.m. Hg. Under such conditions, inhibitor concentrations from about 100 to about 2,000 ppm are suitable with concentrations of from about 300 to about 1,000 ppm being preferred.

The NMA may be introduced into the distillation apparatus in any convenient manner which permits efficient distribution of such substance throughout the distillation apparatus. The manner of introduction is not critical so long as it is intimately distributed within the distillation mixture. One of the primary advantages of utilizing NMA as a polymerization inhibitor is its ease of handling due to its liquid state and infinite solubility in ethylenically unsaturated compounds. Other nitroso compounds of at least equal polymerization inhibiting efficiency do not possess this advantage. For example, although NPH is a very efficient polymerization inhibitor, it is a solid material, not soluble in styrene. Consequently, severe handling problems are encountered in achieving an intimate distribution of NPH within the distillation mixture. NDMA, while infinitely soluble in, for example, styrene and therefore easy to use, has a green color which can produce a dyeing effect on the distillation product. Furthermore, NDMA is not as efficient in inhibiting polymerization of ethylenically unsaturated compounds as is generally desired.

Although NMA alone may be added directly to the distillation mixture, in one embodiment of the present invention, the NMA, prior to being introduced into the distillation mixture, is mixed with a heavy aromatic hydrocarbon fraction having a higher boiling point than the ethylenically unsaturated compound which is to be distilled. The ratio of NMA to the heavy aromatic hydrocarbon fraction can vary widely. Inhibitor to heavy aromatic hydrocarbon ratios between about 1 to 100, preferably 1 to 5, have generally proven suitable, depending on the rate of throughput at which the distillation apparatus is operated. The boiling point of the heavy aromatic hydrocarbon fraction should be at least about 20° F higher than the boiling point of the ethylenically unsaturated compound which is to be distilled. Suitable heavy aromatic hydrocarbon fractions include paraffins and polyalkylbenzenes such as polyethylbenzenes, i.e., diethylbenzene.

After NMA is dissolved in heavy aromatic fraction, the heavy aromatic hydrocarbon fraction is introduced into the distillation mixture. The principal advantage to this embodiment is that the higher boiling heavy aromatic accumulates in the reboiler area of the distillation apparatus and forms a liquid bottoms material having a higher heat content than would liquid bottoms consisting substantially of only the lower boiling ethylenically unsaturated compound being distilled. The higher heat content of the heavy aromatic bottoms enables a shorter residence time in the high heat bottoms area for the readily polymerizable unsaturated compound being distilled and a consequent reduction in the amount of polymerization occurring in the bottom area. Still further, the shorter residence time enables the distillation apparatus to be operated at a higher distillation mixture throughput.

When the process of the present invention is utilized, the bottoms material which accumulates during the distillation process can be drawn off and utilized for its heating value or for reprocessing. When utilizing the commonly used prior art method for vacuum distillation of readily polymerizable ethylenically unsaturated compounds employing sulfur as the polymerization inhibitor, or sulfur in combination with other chemical polymerization inhibitors, a bottoms material is formed which is valueless for further use and constitutes a high pollution waste material which must be disposed of.

Upon recovery of the distillation product obtained in accordance with the present invention. It is found that a higher percentage of the pure readily polymerizable unsaturated compound is recovered in an unpolymerized state. Particularly, when employing the present invention in its preferred application to separate readily polymerizable unsaturated compounds such as divinylbenzene or styrene, it is found that substantially less polymerized material is contained in the distillation apparatus and in the distillation product.

In order to more fully describe and to exemplify the present invention, the following examples are presented. These examples are not to be construed as in any manner limiting the present invention.

EXAMPLE I 100 grams of freshly distilled styrene was inhibited with 500 ppm by weight NMA. The sample was placed in a pressure bottle and purged with nitrogen to remove the dissolved oxygen (air). The pressure bottle was then sealed, placed in a hot oil bath and held at 224° F for 4¼ hours. At the end of this time period, the sample was analyzed and found to contain only 0.45% by weight of polymer.

EXAMPLE II

The same procedure was followed as in Example I except in this case the styrene was inhibited with 400 ppm by weight NMA. The amount of polymer formed after 4¼ hours at 224° F was 0.63% by weight.

EXAMPLE III 100 grams of freshly distilled styrene was inhibited with 1,000 ppm by weight sulfur. The sample was purged with nitrogen, sealed and placed in a hot oil bath at 224° F for 4¼ hours. At the end of this test period the sample was analyzed and found to contain 1.5% by weight of polymer.

EXAMPLE IV

A sample of 1,500 grams of freshly distilled styrene was inhibited with 500 ppm by weight NMA. The sample was refluxed in a 1" ten tray oldershaw column at reduced pressure and at a temperature of 210° F for a period of 4¼ hours. At the end of the test period the styrene was analyzed and found to contain 0.40% by weight of polymer.

What is claimed is:

1. A process for the distillation of a readily polymerizable aromatic hydrocarbon having ethylenically unsaturated substituents which comprises subjecting such compound to distillation conditions in the presence of N,N-nitroso-methylaniline as a polymerization inhibitor in a system from which oxygen and sulfur have been excluded.

2. The method as defined in claim 1 wherein the readily polymerizable aromatic hydrocarbon compound is styrene.

3. The method as defined in claim 1 wherein the readily polymerizable aromatic hydrocarbon compound is divinylbenzene.

4. The method as defined in claim 1 wherein the N,N-nitroso-methylaniline is first dissolved in a heavy aromatic hydrocarbon fraction having a higher boiling point than the aromatic hydrocarbon compound being distilled and said heavy aromatic hydrocarbon fraction containing the dissolved N,N-nitroso-methylaniline is then introduced into said aromatic hydrocarbon compound in the feed stream of said distillation process.

5. The method as defined in claim 3 wherein the N,N-nitroso-methylaniline is dissolved in a heavy aromatic hydrocarbon fraction having a boiling point at least about 20° F higher than the boiling point of the ethylenically unsaturated compound being distilled.

6. The method as defined in claim 5 wherein the heavy hydrocarbon fraction having a boiling point at least about 20° F higher than the boiling point of the ethylenically unsaturated compound being distilled is one containing aromatic hydrocarbons having greater than two substituents to the aromatic nucleus.

7. The process as defined in claim 1, wherein said N,N-nitroso-methylaniline is present in an amount of from about 100 ppm to about 2,000 ppm.

* * * * *